(12) United States Patent
Blumenfeld et al.

(10) Patent No.: US 9,670,159 B2
(45) Date of Patent: Jun. 6, 2017

(54) PHARMACEUTICAL COMPOSITION OF A PAPILLOMAVIRUS INHIBITOR

(71) Applicant: AVIRAGEN THERAPEUTICS, INC., Alpharetta, GA (US)

(72) Inventors: Marta Blumenfeld, Paris (FR); Delphine Compere, Sceaux (FR); Patricia Francon, Bois le Roi (FR); Michel Hutin, Cernay la Ville (FR)

(73) Assignee: AVIRAGEN THERAPEUTICS, INC., Alpharetta, GA (US)

( * ) Notice: Subject to any disclaimer, the term of this patent is extended or adjusted under 35 U.S.C. 154(b) by 0 days.

(21) Appl. No.: 14/399,354

(22) PCT Filed: May 7, 2013

(86) PCT No.: PCT/EP2013/059475
§ 371 (c)(1),
(2) Date: Nov. 6, 2014

(87) PCT Pub. No.: WO2013/167583
PCT Pub. Date: Nov. 14, 2013

(65) Prior Publication Data
US 2015/0152051 A1 Jun. 4, 2015

(30) Foreign Application Priority Data

May 7, 2012 (FR) ..................................... 12 54186

(51) Int. Cl.
*C07D 211/34* (2006.01)
*A61K 9/00* (2006.01)
*A61K 47/26* (2006.01)
*A61K 9/06* (2006.01)
*A61K 31/4453* (2006.01)
*C07D 295/135* (2006.01)

(52) U.S. Cl.
CPC .......... *C07D 211/34* (2013.01); *A61K 9/0014* (2013.01); *A61K 9/06* (2013.01); *A61K 31/4453* (2013.01); *A61K 47/26* (2013.01); *C07D 295/135* (2013.01); *A61K 9/0034* (2013.01)

(58) Field of Classification Search
None
See application file for complete search history.

(56) References Cited

U.S. PATENT DOCUMENTS

2009/0209586 A1* 8/2009 Blumenfeld ....... C07D 295/135
514/331
2010/0286162 A1* 11/2010 Blumenfeld ....... C07D 295/205
514/252.13

FOREIGN PATENT DOCUMENTS

WO   WO 2007/135106 A1   11/2007
WO   WO 2009/065893 A1    5/2009

OTHER PUBLICATIONS

Rowe, Raymond C., Paul J. Sheskey, and Marian E. Quinn, EDS. Handbook of Pharmaceutical Excipients, London: Pharmaceutical press, 2009, pp. 317-322 (Hydoxypropyl Cellulose), and pp. 592-594 (Propylene Glycol).*
Chiang et al., "Viral E1 and E2 proteins support replication of homologous and heterologous papillomaviral origins," Proc. Natl. Acad. Sci. USA, vol. 89, pp. 5799-5803, Jul. 1992.
White et al., "Inhibition of Human Papillomavirus DNA Replication by Small Molecule Antagonists of the E1-E2 Protein Interaction," The Journal of Biological Chemistry, vol. 278, No. 29, pp. 26765-26772, Jul. 18, 2003.
Fradet-Turcotte et al., "Development of Quantitiative and High-Throughput Assays of Polyomavirus and Papillomavirus DNA Replication," Virology, vol. 399, No. 1, pp. 65-76, Mar. 30, 2010.
International Search Report issued in application No. PCT/EP2013/059475 on Oct. 2, 2013.

* cited by examiner

*Primary Examiner* — Timothy R Rozof
(74) *Attorney, Agent, or Firm* — B. Aaron Schulman, Esq.; Stites & Harbison, PLLC

(57) ABSTRACT

The invention relates to a pharmaceutical composition including a compound of general formula (I) combined with a solvent and a viscosity-enhancing agent, as well as to the use thereof as a drug, in particular for treating and preventing infection with the papillomavirus, and to the method for preparing same.

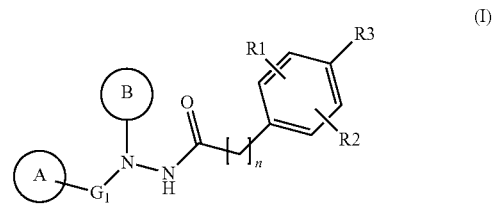

26 Claims, 1 Drawing Sheet

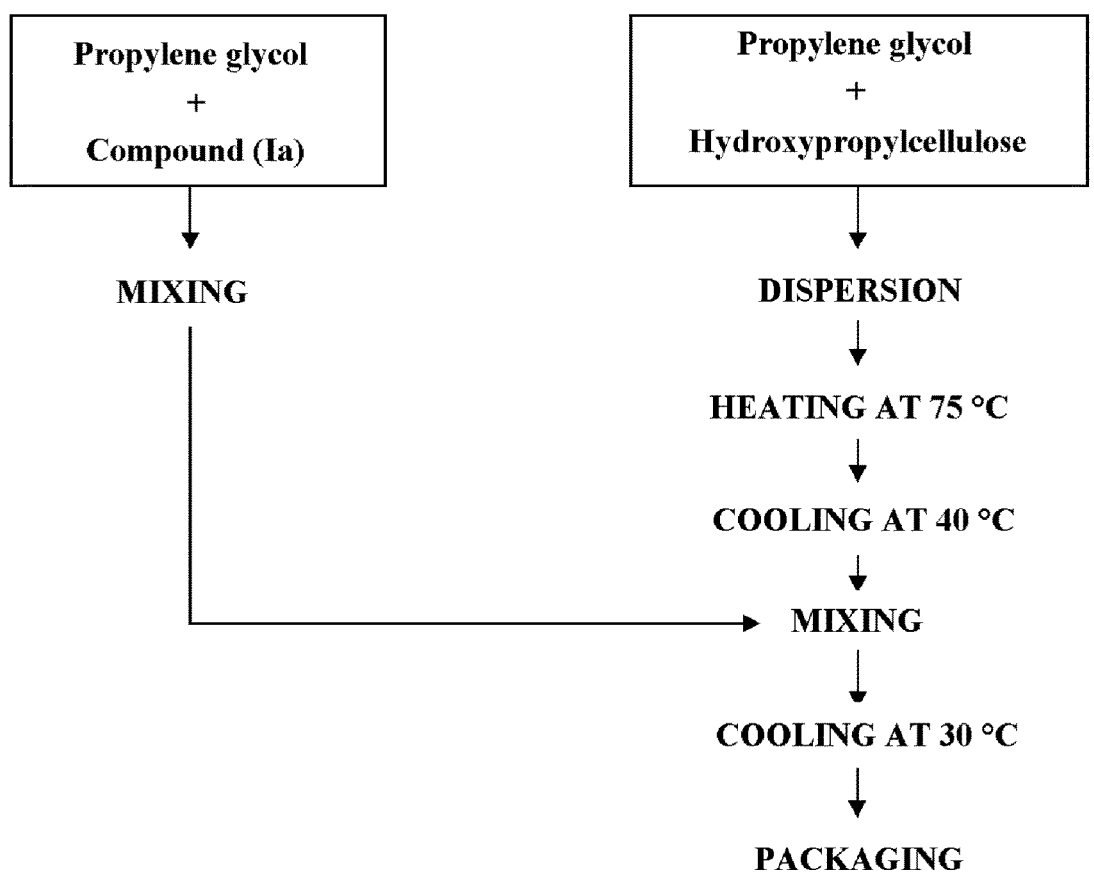

PHARMACEUTICAL COMPOSITION OF A PAPILLOMAVIRUS INHIBITOR

The present invention relates to a pharmaceutical composition of compounds useful for treating and preventing infections linked to papillomavirus, described in particular in the application WO 2007/135106.

The compounds described in the application WO 2007/135106 have the following structure:

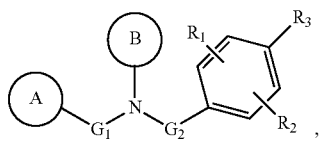

wherein:
  A represents an aryl, cycloalkyl, cycloalkenyl or heterocycle group, optionally substituted,
  B represents an aryl or heterocycle, optionally substituted
  R1 and R2 represent independently a hydrogen atom or various substituents,
  R3 represents an acid functional group or a radical prodrug or bioisostere of this functional group,
  $G_1$ represents a bond or a hydrocarbon chain, and
  $G_2$ represents a

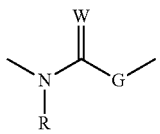

group, with R representing a hydrogen atom or various substituents, W representing O, S or NH and G representing a bond or a hydrocarbon chain.

However, no formulation of these compounds is described in WO 2007/135106.

These compounds useful in treating and preventing infections linked to papillomavirus are intended in particular to be applied topically to the skin and mucous membranes, in particular in the anogenital region.

The inventors thus discovered that very simple to prepare pharmaceutical compositions enabled quick and high release of the active ingredient.

The present invention thus has as an object a pharmaceutical composition including a compound of general formula (I):

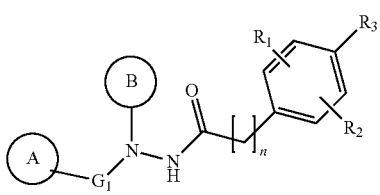

or a pharmaceutically acceptable salt thereof,
wherein:
  $G_1$ represents a bond or a linear or branched, saturated or unsaturated hydrocarbon chain comprised of 1 to 4 carbon atoms, optionally substituted by one or two alkyl groups, preferably identical,
  A represents an aryl group, such as phenyl, optionally substituted:
    in the meta or para position by:
      a halogen atom or a cyano, alkoxy, haloalkoxy, acylaminoalkyl or —XR group where X represents —O—, —S—, —SO—, —SO$_2$— or —CO— and R represents an arylalkyl, cycloalkyl or aryl group, each one optionally substituted by one or two substituents, identical or different, such as a halogen atom, alkoxy or acyl group, or
      a cycloalkyl, aryl or arylalkyl group, each one optionally substituted by one or two substituents, identical or different, such as an acyl or alkoxy group,
    and/or in the ortho or meta position by an alkyl group,
  B represents an aryl group, preferably a phenyl, substituted in the ortho position by a heterocycle, preferably an N-cycloalkyl, such as a piperidin-1-yl group, and optionally substituted in the ortho' position by an alkyl group, such as a methyl,
  n is an integer between 1 and 4, preferably between 1 and 2, and more preferably is 1,
  R1 represents an alkoxy group, such as methoxy, preferably in the ortho position in relation to R3,
  R2 represents a hydrogen or halogen atom, such as chlorine or bromine, or an alkyl group, such as methyl, preferably in the meta position in relation to R3, and
  R3 represents an acid or ester group, and preferably acid,
in combination with a viscosity-enhancing agent.

In the present invention, what is meant by "pharmaceutically acceptable" is that which is useful in preparing a pharmaceutical composition which is generally safe, non-toxic and neither biologically nor otherwise undesirable and which is acceptable for veterinary use as well as human pharmaceutical use.

By "pharmaceutically acceptable salts" of a compound is meant in the present invention salts which are pharmaceutically acceptable, as defined herein, and which have the desired pharmacological activity of the parent compound. Such salts include:
(1) hydrates and solvates,
(2) acid addition salts formed with inorganic acids such as hydrochloric acid, hydrobromic acid, sulfuric acid, nitric acid, phosphoric acid and the like; or formed with organic acids such as acetic acid, benzenesulfonic acid, benzoic acid, camphorsulfonic acid, citric acid, ethane-sulfonic acid, fumaric acid, glucoheptonic acid, gluconic acid, glutamic acid, glycolic acid, hydroxynaphthoic acid, 2-hydroxyethanesulfonic acid, lactic acid, maleic acid, malic acid, mandelic acid, methanesulfonic acid, muconic acid, 2-naphthalene-sulfonic acid, propionic acid, salicylic acid, succinic acid, dibenzoyl-L-tartaric acid, tartaric acid, p-toluenesulfonic acid, trimethylacetic acid, trifluoroacetic acid and the like; and
(3) salts formed when an acid proton present in the parent compound either is replaced by a metal ion, for example an alkali metal ion (Na$^+$, K$^+$ or Li$^+$ for example), an alkaline-earth metal ion (such as Ca$^{2+}$ or Mg$^{2+}$) or an aluminum ion; or is coordinated with an organic or inorganic base. Acceptable organic bases include diethanolamine, ethanolamine, N-methylglucamine, triethanolamine, tromethamine and the like. Acceptable inorganic bases include aluminum hydroxide, calcium hydroxide, potassium hydroxide, sodium carbonate and sodium hydroxide.

It will be in particular an alkali metal salt, and in particular a potassium salt.

By "unsaturated" is meant, in the context of the present invention, that the group includes one or more unsaturations.

By "unsaturation" is meant, in the context of the present invention, a double bond or a triple bond.

By "halogen" is meant, in the context of the present invention, a fluorine, bromine, chlorine or iodine atom. Advantageously, it is a fluorine, bromine or chlorine atom.

By "alkyl" group is meant, in the context of the present invention, a linear or branched saturated hydrocarbon chain comprising from 1 to 6 carbon atoms, in particular the following groups: methyl, ethyl, n-propyl, isopropyl, n-butyl, isobutyl, sec-butyl, tert-butyl, n-pentyl or n-hexyl. Advantageously, it is methyl.

By "cycloalkyl" group is meant, in the context of the present invention, a saturated monocyclic or polycyclic system, preferably mono-, bi- or tricyclic, comprising from 3 to 12 carbon atoms, the rings being able to be fused or bridged in pairs, such as the following groups: cyclopropyl, cyclopentyl, cyclohexyl, cycloheptyl, cyclooctyl, adamantyl, decalinyl or norbornyl.

By "N-cycloalkyl" group is meant, in the context of the present invention, a cycloalkyl group as defined above wherein a carbon atom has been substituted by a nitrogen atom, the bond with the molecule being made by this nitrogen atom. It is advantageously a piperidin-1-yl or pyrrolidin-1-yl group.

By "acyl" group is meant, in the context of the present invention, a group of formula —C(O)—Z, where Z represents an alkyl group as defined above or a phenyl. It may be advantageously an acetyl, ethylcarbonyl or benzoyl group.

By "alkoxy" group is meant, in the context of the present invention, an alkyl group as defined above linked to the molecule via an oxygen atom. It may be in particular a methoxy, ethoxy, n-propoxy, isopropoxy, n-butoxy, iso-butoxy, sec-butoxy or tert-butoxy group.

By "haloalkoxy" group is meant, in the context of the present invention, an alkoxy group as defined above substituted by at least one halogen atom as defined above. Preferably, it will be fluoroalkoxy, i.e. an alkoxy group substituted by at least one fluorine atom such as a —OCF$_3$ or —OCH$_2$CF$_3$ group.

By "aryl" group is meant, in the context of the present invention, an aromatic group comprising preferably from 5 to 10 carbon atoms and including at least one joined ring, such as, for example, a phenyl or naphthyl group. Advantageously, it is phenyl.

By "heterocycle" is meant, in the context of the present invention, a saturated, unsaturated or aromatic monocyclic or polycyclic system, and preferably mono- or bi-cyclic, comprising from 3 to 12 members, the rings being able to be fused, spiro or bridged in pairs, and including 1 to 4 heteroatoms, identical or different, selected from O, S and N, and optionally including one or two oxo or thioxo groups, with it being understood that in the case of a polycyclic system one of the rings may be aromatic while the others may be aromatic, saturated or unsaturated. Advantageously, it relates to the following groups: piperidyl, piperazyl, furyl, thienyl, pyrrolyl, pyrazolyl, imidazolyl, pyridyl, pyrimidyl, pyrazinyl, pyradizinyl, benzofuryl, benzothienyl, indolyl, quinolyl, isoquinolyl, benzodioxolyl, benzodioxinyl, benzo[1,2,5]thiadiazolyl, benzo[1,2,5]oxadiazolyl, [1,2,3]triazolyl and [1,2,4]triazolyl.

By "arylalkyl" group is meant, in the context of the present invention, an aryl group as defined above linked to the molecule via an alkyl group as defined above. Preferably, it is a benzyl group.

By "acylaminoalkyl" is meant, in the context of the present invention, a group of formula -Alk-NHCO-Alk', where Alk and Alk' represent, independently of each other, an alkyl group as defined above.

By "acid" is meant, in the context of the present invention, a COOH group.

By "ester" is meant, in the context of the present invention, a —CO—O-Alk group, where Alk represents an alkyl group as previously defined.

By "viscosity-enhancing agent" is meant, in the context of the present invention, a compound which increases the viscosity of a fluid, such as a liquid. It thus changes the rheological properties of the fluid which then becomes more viscous.

Advantageously, the composition according to the invention will include 0.01 to 10%, in particular 2 to 8%, preferably about 5% by weight of a compound of formula (I) in relation to the total weight of the composition.

The viscosity-enhancing agent may be hydroxypropylcellulose, hydroxypropylmethylcellulose or a carbomer. The viscosity-enhancing agent may also be in the form of a mixture of these. Preferably, the viscosity-enhancing agent will be hydroxypropylcellulose.

The composition according to the invention may include 0.01 to 50%, in particular 0.05 to 10%, notably 0.5 to 5%, preferably 1 to 5% by weight of this viscosity-enhancing agent in relation to the total weight of the composition.

The composition according to the invention will advantageously further include a solvent such as propylene glycol, glycerol, or polyethylene glycol. The solvent may also be in the form of a mixture of these. Preferably, the solvent will be propylene glycol.

The composition according to the invention may include 40 to 99.9%, in particular 80 to 99.5%, notably 85 to 99%, preferably 90 to 95% by weight of this solvent in relation to the total weight of the composition.

Thus, the composition according to the present invention advantageously will include, and preferably will be comprised of, a compound of formula (I), a viscosity-enhancing agent and a solvent.

This pharmaceutical composition may in particular include or be comprised of (percentages by weight being expressed in relation to the total weight of the pharmaceutical composition):
  0.01 to 10%, in particular 2 to 8% by weight of the compound of formula (I),
  0.01 to 50%, in particular 0.05 to 10%, notably 0.5 to 5%, preferably 1 to 5% by weight of viscosity-enhancing agent, and
  40 to 99.9%, in particular 80 to 99.5%, notably 85 to 99%, preferably 90 to 95% by weight of solvent.

Advantageously, this pharmaceutical composition will include or will be comprised of (percentages by weight being expressed in relation to the total weight of the pharmaceutical composition):
  0.01 to 10%, in particular 2 to 8%, and preferably about 5% by weight of the compound of formula (I),
  0.05 to 10%, in particular 0.5 to 5%, notably 1 to 5%, preferably about 3% by weight of a viscosity-enhancing agent selected from hydroxypropylcellulose, ydroxypropylmethylcellulose, a carbomer and mixtures thereof, and 80 to 99.5%, in particular 85 to 99%, notably 90 to 95%, preferably about 92% by weight of a solvent selected from propylene glycol, glycerol, polyethylene glycol and mixtures thereof.

Preferably, the composition according to the present invention will include, and preferably will be comprised of, a compound of formula (I), hydroxypropylcellulose and propylene glycol.

This composition according to the invention will thus have in particular the following composition, in relation to the total weight of the composition:
- 0.01 to 10%, in particular 2 to 8%, preferably about 5% by weight of a compound of formula (I),
- 0.01 to 50%, in particular 0.05 to 10%, notably 0.5 to 5%, notably 1 to 5%, preferably about 3% by weight of hydroxypropylcellulose, and
- 40 to 99.9%, in particular 80 to 99.5%, notably 85 to 99%, notably 90 to 95%, preferably about 92% by weight of propylene glycol.

The composition according to the invention will be provided in particular in gel form.

In this case, the gel will have in particular a viscosity of 5,000 to 50,000 mPa·s, in particular 15,000 to 25,000 mPa·s, measured according to the European Pharmacopoeia 2.2.10 standards. Viscosity is measured more particularly at 25° C. using a Brookfield model HDBV+ apparatus or equivalent, with a no. 21 spindle for a speed of 10 rpm. The values are given after 1 minute of rotation.

Advantageously, G1 represents a bond or a linear and saturated hydrocarbon chain composed of 1 to 4 carbon atoms, and preferably represents a bond.

In an advantageous manner, the radical A defined above is an aryl, preferably a phenyl, substituted in the meta or para position, preferably para, by an alkoxy group, such as methoxy, or by an aryl or arylalkyl group, such as phenyl or benzyl, optionally substituted by one or two substituents, identical or different, such as an acyl or alkoxy group.

Advantageously, B represents an aryl group, preferably a phenyl, substituted in the ortho position by a heterocycle, preferably an N-cycloalkyl, such as a piperidin-1-yl group, and optionally substituted in the ortho' position by an alkyl group, such as a methyl.

Advantageously, R2 represents a halogen atom, such as a bromine atom, preferably in the meta position in relation to R3.

Preferably, the compound of formula (I) has the following characteristics:
- A represents a phenyl group substituted in the para position by a benzyl group,
- B represents a phenyl group substituted in the ortho position by a piperidin-1-yl group and in the ortho' position by a methyl group,
- G1 represents a bond, and
- R1, R2, R3 and n are as previously defined.

In particular, the compound of formula (I) is 4-[N'-(4-benzyl-phenyl)-N'-(2-methyl-6-piperidin-1-yl-phenyl)-hydrazinocarbonylmethyl]-5-bromo-2-methoxy-benzoic acid or a pharmaceutically acceptable salt thereof, and in particular the potassium salt thereof.

Indeed, the potassium salt increases the solubility of this compound, in particular in comparison with its hydrochloride, and facilitates the formulation of the product.

The present invention thus also has as an object the potassium salt of 4-[N'-(4-benzyl-phenyl)-N'-(2-methyl-6-piperidin-1-yl-phenyl)-hydrazinocarbonylmethyl]-5-bromo-2-methoxy-benzoic acid.

The present invention also relates to this particular salt for use as a drug, in particular to prevent or treat papillomavirus infection, and in particular HPV6 or HPV11 infection.

This potassium salt enables in particular the prevention or treatment of lesions or diseases associated with papillomavirus infections, and in particular anogenital warts, such as condyloma acuminata and condyloma lata, laryngeal, conjunctival or oral papillomas, recurrent respiratory papillomatosis, low-grade and high-grade intraepithelial neoplasia, bowenoid papulosis, common, plantar, myrmecia, superficial or flat warts, epidermodysplasia verruciformis, and carcinomas, in particular anogenital.

It will be notably useful for treating lesions caused in particular by HPV6 and HPV11 infections, in particular warts and condylomas.

The present invention also relates to any pharmaceutical composition including this potassium salt in combination with at least one pharmaceutically acceptable excipient.

The present invention also has as an object a composition according to the present invention for use as a drug, in particular to prevent or treat papillomavirus infection, and in particular HPV6 or HPV11 infection.

The present invention also relates to the use of a composition according to the invention for preparing a drug useful in preventing or treating papillomavirus infection, and in particular HPV6 or HPV11 infection.

The present invention also relates to a method for preventing or treating papillomavirus infection, and in particular HPV6 or HPV11 infection, comprising the administration of an effective quantity of a composition according to the invention to a person in need thereof.

The composition will in particular be used topically, in particular in gel form; oral administration may also be envisaged.

By "topically" is meant, in the context of the present invention, local application. This application may be carried out on the skin or on the mucous membranes (external or internal) such as the respiratory tract, the oral cavity or the anogenital region. It may also be carried out by local injection in or around a lesion or tumor. Preferably, it is carried out on the skin and/or the mucous membranes, and in particular in the anogenital region.

The composition according to the present invention enables in particular the prevention or treatment of lesions or diseases associated with papillomavirus infections, and in particular anogenital warts, such as condyloma acuminata and condyloma lata, laryngeal, conjunctival or oral papillomas, recurrent respiratory papillomatosis, low-grade and high-grade intraepithelial neoplasia, bowenoid papulosis, common, plantar, myrmecia, superficial or flat warts, epidermodysplasia verruciformis, and carcinomas, in particular anogenital.

The composition according to the present invention will in particular be useful for treating lesions caused notably by HPV6 and HPV11 infections, in particular warts and condylomas.

The compositions according to the present invention may be prepared by mixing the various ingredients.

The present invention thus also has as an object a method for preparing a composition according to the present invention including a compound of formula (I), a viscosity-enhancing agent and a solvent, comprising the following steps:

i) mixing the compound of formula (I) in part of the solvent to yield a solution A,
ii) mixing the viscosity-enhancing agent in the remaining part of the solvent to yield a solution B, and
iii) mixing solutions A and B to yield the composition according to the invention.

Preferably, step (i) will be carried out at room temperature.

Preferably, step (ii) will be carried with heat to obtain a homogeneous solution of the viscosity-enhancing agent. This step will be carried out in particular at a temperature between 60 and 100° C., preferably between 70 and 80° C. Solution B will then be cooled before being used in step (iii).

Preferably, step (iii) will be carried out at a temperature between 20 and 40° C. In this case, the reactor containing solution A will be emptied into the reactor containing solution B, or vice versa. The reactor thus emptied may further be rinsed with a little solvent according to standard practice.

The present invention will be better understood in the light of the nonrestrictive examples which follow.

FIGURE

FIG. 1 represents the diagram of the method for manufacturing a composition according to the invention.

EXAMPLES

The active ingredient used in the examples is the potassium salt of 4-[N'-(4-benzyl-phenyl)-N'-(2-methyl-6-piperidin-1-yl-phenyl)-hydrazinocarbonylmethyl]-5-bromo-2-methoxy-benzoic acid (compound (Ia)).

One method of obtaining the potassium salt of the active ingredient is based on the transformation of the neutral form of the compound of interest solubilized in ethanol with ethanolic potassium hydroxide. The neutral form is itself obtained from the washing with water of the compound in hydrochloride form as claimed in the patent WO 2007/135106.

Compositions According to the Invention with 5% by Weight of Active Ingredient in Gel Form

| Components | Percent composition (% by weight) | | | | | | |
|---|---|---|---|---|---|---|---|
| Pharmaceutical composition | (a) | (b) | (c) | (d) | (e) | (f) | (g) |
| Compound (Ia) | 5.00 | 5.00 | 5.00 | 5.00 | 5.00 | 5.00 | 5.00 |
| Propylene glycol | 94.2 | 94.0 | 93.8 | 93.5 | 93.5 | 93.0 | 92.0 |
| Klucel ® (Hydroxypropyl-cellulose) | 0.8 | 1.0 | 1.2 | 1.5 | 1.5 | 2.0 | 3.0 |
| Klucel ® grade | MF-Pharm | MF-Pharm | MF-Pharm | MF-Pharm | MXF-Pharm | GF-Pharm | GF-Pharm |

The pharmaceutical composition is a gel containing 5% by weight of compound (Ia).

Hydroxypropylcellulose:

The specifications are those of the European Pharmacopoeia monograph no. 0337.

The source of the hydroxypropylcellulose is Klucel® resold by the supplier ASHLAND with the following grades: MF-Pharm, MXF-Pharm and GF-Pharm.

Propylene Glycol:

The specifications are those of the European Pharmacopoeia monograph no. 0430.

Manufacture of Pharmaceutical Compositions (a) to (g)

The active ingredient (Ia) is dissolved in a fraction of propylene glycol. Hydroxypropylcellulose is dispersed in propylene glycol "cold" and the mixture is then heated to obtain the dissolution of the viscosity-enhancing agent. When the gel is cooled to 40° C., the solution of active ingredient (Ia) in propylene glycol is added (the container having contained this solution is rinsed with a little propylene glycol) and the mixture is homogenized. Stirring is maintained until room temperature is reached.

The method for manufacturing the gel is presented in FIG. 1.

The following 5,000 g batch (corresponding to composition (g)) was in particular prepared according to this method:

| Ingredients | % | Quantity for a 5,000 g batch |
|---|---|---|
| Active ingredient: | | |
| Compound (Ia) | 5% | 250 g |
| Excipients: | | |
| Hydroxypropylcellulose* | 3% | 150 g |
| Propylene glycol | 92% | qs 5000 g |

*KLUCEL ® GF-Pharm

The active ingredient is dissolved at room temperature in about 750 g of propylene glycol for a 5,000 g batch of gel. The hydroxypropylcellulose is dispersed in about 3,600 g of propylene glycol. The mixture is heated with stirring at 75±5° C. until a homogeneous gel is obtained. The preparation is left to cool to 40° C. or lower while maintaining stirring.

With stirring, the active ingredient in solution is poured into the hydroxypropylcellulose in solution and the container with the remaining propylene glycol (about 250 g) is rinsed. The final gel is left to cool to 30±5° C. with stirring before being packaged.

The pharmaceutical composition obtained is a viscous, translucent, colorless to light yellow gel.

Study of Diffusion Through a Synthetic Membrane of the Active Ingredient from Pharmaceutical Composition (d)

Studies of diffusion through a synthetic dialysis membrane made of cellulose mounted on a Franz diffusion cell were carried out with pharmaceutical composition (d).

The diffusion kinetics of compound (Ia) through the membrane were monitored for 6 hours. When the kinetics stopped, more than 20% of the active ingredient was released from the pharmaceutical composition.

Biological Activity of the Pharmaceutical Composition

The activity against papillomavirus of an active ingredient can be evaluated in various in vitro and cellular tests such as those described by Chiang et al. (1992), *Proc. Natl. Acad. Sci. USA*, 89:5799-5803, by White et al. (2003), *Journal of Biological Chemistry*, 278:26765-26772, or by Fradet-Turcotte et al. (2010), Virology, 399:65-76.

In the present invention two types of tests are used to study the biological activity of compounds against papillomavirus. A first test ("E1/E2 interaction test") evaluates the interaction between the E1 and E2 proteins of HPV (human papillomavirus) in human cells. A second test ("replication test") measures the replication of viral genomic DNA in human cells.

Interaction Test

The test of interaction between E1 and E2 is similar to the tests often called "mammalian two-hybrid" tests. It is based on co-transfection of a reporter vector containing DNA binding sites for the E2 protein of HPV in the promoter controlling expression of the reporter gene, and of expression vectors coding the E1 and E2 proteins of HPV, the E1 protein being fused to the VP16 transactivation domain. This test makes it possible to follow the interaction between the E1 and E2 proteins, this interaction being a step required for replication of the genome of HPVs.

For the tests of interaction between E1 and E2, a reporter vector containing several DNA binding sites for the E2 protein (the palindrome 5' ACCGNNNNCGGT-3') upstream from the minimal adenovirus major-late promoter (MLP) controlling transcription of the gene coding firefly luciferase was constructed. HPV E1 protein expression vectors fused at the N-terminal with the VP16 transactivation domain of HSV-1 were also constructed. Co-transfection in cell lines of this reporter vector containing E2 sites and HPV E2 protein expression vectors results in a marginal increase in luciferase activity. Co-transfection of this reporter vector containing E2 sites, HPV E2 protein expression vectors and E1 protein expression vectors fused to the VP16 domain enables formation in the cells of the strongly transactivating E2/E1-VP16 protein complex, and results in a large increase in luciferase activity. This expresses the interaction between the E1 and E2 proteins in the cells.

Replication Test

The test of replication of viral genomic DNA is based on the co-transfection of a reporter vector containing an HPV origin of replication (ori) and expression vectors coding the E1 and E2 proteins of HPV. It makes it possible to follow the set of biological functions of E1 and E2 required for replication of the genome of the HPVs.

For the tests of viral genomic DNA replication, a "replicon" reporter vector containing the HPV11/HPV6 origin of replication (also called LCR, which carries the binding sites of the E1 and E2 proteins of HPV) and the gene coding firefly luciferase under the transcriptional control of the SV40 promoter was constructed. It was verified that the presence of the HPV origin of replication has no transcriptional effect on expression of the luciferase gene, this either in the presence or in the absence of the E1 or E2 viral proteins. Co-transfection of this replicon-vector and HPV E1 and E2 protein expression vectors in human cell lines results in an increase in luciferase activity that is dependent on the presence of E1 and E2, expressing the increase in the number of reporter vectors. This is due to the activity of the E1 and E2 viral proteins which allow replication in mammalian cells of this replicon-vector containing a viral origin of replication.

In order to show that the formulation of the active ingredient in the pharmaceutical composition according to the invention does not change the biological activity of the non-formulated active ingredient, the activity of compound (Ia) was measured by studying the biological activity against papillomavirus, either of pharmaceutical compositions (a), (d), (f) and (g) according to the invention, or of compound (Ia) in freshly prepared Tris-DMSO buffer solution (25 mM Tris, pH 8.0, 5% DMSO).

Pharmaceutical compositions (a), (d), (f) and (g) were diluted in the same buffer solution to be tested at the same concentrations as the active ingredient, namely in a range of 0.25 to 40 µM.

Compound (Ia), either in solution or in pharmaceutical compositions (a), (d), (f) and (g), was evaluated for its inhibitory activity on the interaction between the E1 and E2 proteins of HPV11/HPV6 in human cell lines derived from renal epithelial cells or cervical carcinoma cells. Various doses (0.25-40 µM) were incubated in the cell medium for 2 days after transfection, and luciferase activity was measured to determine the $IC_{50}$ of the compound on the interaction between the E1 and E2 proteins of the HPVs.

Compound (Ia), either in solution or in pharmaceutical compositions (a), (d), (f) and (g), was also evaluated for its inhibitory activity on the E1- and E2-dependent viral replication of HPV11/HPV6 in human cell lines derived from renal epithelial cells or cervical carcinoma cells. Various doses (0.25-40 µM) were incubated in the cell medium for 2 to 6 days after transfection, and luciferase activity was measured using a luminometer to determine the $IC_{50}$ of the compound on the replication of the genome of the HPVs.

The pharmaceutical compositions described above exhibit the same biological activity as compound (Ia) in solution (non-formulated). Compound (Ia) in solution and pharmaceutical compositions (a), (d), (f) and (g) inhibit both the interaction between HPV11/HPV6 E1 and E2 proteins in cells and E1 and E2 protein-dependent viral replication of HPV11 in cells, with an $IC_{50}$ of about 1 µM.

Percutaneous Absorption In Vitro and In Vivo

The percutaneous absorption of compound (Ia) from pharmaceutical composition (g) was studied after the application of a dose of 10 mg/cm² on human skin mounted on a Franz cell. This study was carried out by comparing percutaneous absorption on healthy skin and on delaminated skin, as a model of the weak keratinization of the anogenital region.

After 8 or 24 hours of exposure to pharmaceutical composition (g), the quantity of compound (Ia) present in each skin layer (stratum corneum, epidermis, dermis) and that having crossed the skin (receiving fluid) is quantified by HPLC.

The results obtained after 8 hours of diffusion are presented in the table below.

| | Stratum corneum | Epidermis | Dermis | Receiving fluid |
|---|---|---|---|---|
| | | % of dose applied | | |
| Healthy human skin | 1.40 ± 0.40 | 0.20 ± 0.04 | 0.10 ± 0.04 | 0 |
| Delaminated human skin | NA | 3.20 ± 1.50 | 4.40 ± 1.10 | 0.70 ± 1.20 |

The stratum corneum of the non-delaminated skin samples is removed from the epidermis by peeling with adhesive. The latter is applied to the skin surface under constant and controlled pressure.

NA: not applicable

The concentrations of compound (Ia) measured in the skin after 8 hours of diffusion correspond to a local concentration of 100 times (healthy skin) to 1000 times (delaminated skin) the activity of the active ingredient ($IC_{50}$) measured in cellulo. Similar results were obtained after 24 hours of diffusion. In the same way, similar results were observed in studies of percutaneous absorption in vitro on skin of miniature pig, an animal model highly predictive of the behavior of human skin.

Furthermore, whereas the local concentration of the active ingredient in the skin is high, only a small quantity of compound (Ia) crossed the skin of miniature pig mounted on a Franz cell. About 0.1% of the dose applied was thus measured in the receiving liquid after 24 hours of exposure to a dose of 10 mg/cm² of pharmaceutical composition (g).

The percutaneous absorption of compound (Ia) from pharmaceutical composition (g) was also measured in vivo during a study of toxicokinetics, carried out by twice-daily application for 42 days of a dose of 10 mg/cm² on the flanks of miniature pigs. The presence of compound (Ia) was measured and quantified the first day and the last day of the study in the blood of the treated animals using a very sensitive LC-MS/MS bioanalytical method (limit of detection=0.5 ng/ml). In a way similar to the studies of percutaneous absorption in vitro on human skin and of miniature pig described above, small quantities of compound (Ia) were detected in the blood of the miniature pigs. Thus, about 0.1% of the dose applied was measured, showing low percutaneous absorption in vivo of compound (Ia) from the pharmaceutical composition.

The whole of these results shows a high local concentration of the active ingredient (compound (Ia)) in the skin after application of the pharmaceutical composition and a low systemic exposure of same, as is desired for drugs used topically.

Tolerance

Very good tolerance to pharmaceutical composition (g) was shown in both miniature pig during a preclinical toxicity study and in healthy volunteers during a Phase Ia clinical study. In miniature pig, a dose of 10 mg/cm² was applied twice daily to a 25, 125 or 250 cm² area on the flank of the animals for 42 days. Whatever the area treated, great tolerance to the pharmaceutical composition was observed. Moreover, very good tolerance to the pharmaceutical composition was shown during the twice-daily application for 7 days, at a dose of 10 mg/cm² on a 25 cm² area on the lower back of healthy volunteers. No local reaction or adverse effect was observed in the 8 healthy volunteers treated.

Microbiological Properties

The efficacy of the antimicrobial preservation of pharmaceutical compositions (a) and (g) was tested according to the method of the European Pharmacopoeia (method 5.1.3 with application of standards 5.1.3-2).

The results are presented in the table below:

Pharmaceutical Composition (a):

| Microorganisms | Inoculum CFU*/g | Standards (log reduction) | | | | Results (log reduction) | | | | Conclusion |
|---|---|---|---|---|---|---|---|---|---|---|
| | | 2 d | 7 d | 14 d | 28 d | 2 d | 7 d | 14 d | 28 d | |
| Pseudomonas aeruginosa | 4.2 · 10⁵ | 2 | 3 | — | NI | >4 | >4 | >4 | >4 | Conforms |
| Staphylococcus aureus | 6.0 · 10⁵ | 2 | 3 | — | NI | >3 | >3 | >3 | >3 | Conforms |
| Candida albicans | 5.8 · 10⁵ | — | — | 2 | NI | — | — | >4 | >4 | Conforms |
| Aspergillus niger | 3.3 · 10⁵ | — | — | 2 | NI | — | — | >4 | >4 | Conforms |

NI: no increase
*CFU: colony forming unit

Pharmaceutical Composition (g):

| Microorganisms | Inoculum CFU*/g | Standards (log reduction) | | | | Results (log reduction) | | | | Conclusion |
|---|---|---|---|---|---|---|---|---|---|---|
| | | 2 d | 7 d | 14 d | 28 d | 2 d | 7 d | 14 d | 28 d | |
| Pseudomonas aeruginosa | 2.4 · 10⁵ | 2 | 3 | — | NI | >4 | >4 | >4 | >4 | Conforms |
| Staphylococcus aureus | 3.9 · 10⁵ | 2 | 3 | — | NI | >3 | >3 | >3 | >3 | Conforms |
| Candida albicans | 5.7 · 10⁵ | — | — | 2 | NI | — | — | >4 | >4 | Conforms |
| Aspergillus niger | 6.0 · 10⁵ | — | — | 2 | NI | — | — | >4 | >4 | Conforms |

NI: no increase
*CFU: colony forming unit

The results are in conformity with the A criteria of method 5.1.3-2 of the European Pharmacopoeia.

By means of the presence of propylene glycol, known to persons skilled in the art for its antimicrobial preservative properties, the formulation is protected against microbial contamination and, consequently, does not require additional preservative.

Stability Study

The stability of pharmaceutical composition (g) was studied on a 5 kg laboratory batch.

The following preservation conditions were tested in accordance with ICH recommendations:
- Long-term condition: 5° C.±3° C.,
- Intermediate condition: 25° C.±2° C./60%±5% RH (relative humidity), and
- Accelerated condition: 40° C.±2° C./75%±5% RH.

The test methods are those used routinely and include:
verifying appearance,
measuring viscosity, and
assaying the active ingredient (Ia) by HPLC.

The results obtained are presented in the following tables:

Stability data at 5° C.

| TESTS | STANDARDS AT EXPIRY | T 0 | 1 month | 2 months | 3 months | 6 months | 9 months | 12 months |
|---|---|---|---|---|---|---|---|---|
| Appearance | Translucent, colorless to light yellow | Conforms | Conforms | Conforms | Conforms | Conforms | Conforms | Conforms |
| Viscosity (mPa · s) | — | 18720 | ND | ND | 17040 | 18800 | 16200 | 15400 |
| Content of compound (Ia) (% by weight) | 4.50-5.50% | 5.01 | 5.05 | 4.95 | 4.93 | 4.96 | 5.00 | 4.91 |

ND: not determined

Stability data at 25° C/60% RH

| TESTS | STANDARDS AT EXPIRY | T 0 | 1 month | 2 months | 3 months | 6 months | 9 months | 12 months |
|---|---|---|---|---|---|---|---|---|
| Appearance | Translucent, colorless to light yellow | Conforms | Conforms | Conforms | Conforms | Conforms | Conforms | Conforms |
| Viscosity (mPa · s) | — | 18720 | 19200 | ND | 21040 | 17720 | ND | 15880 |
| Content of compound (Ia) (% by weight) | 4.50-5.50% | 5.01 | 5.02 | 4.93 | 4.95 | 4.92 | 4.99 | 4.87 |

ND: not determined

Stability data at 40° C/75% RH

| TESTS | STANDARDS AT EXPIRY | T 0 | 1 month | 2 months | 3 months |
|---|---|---|---|---|---|
| Appearance | Translucent, colorless to light yellow | Conforms | Conforms | Conforms | Conforms |
| Viscosity (mPa · s) | — | 18720 | ND | ND | 18600 |
| Content of compound (Ia) (% by weight) | 4.50-5.50% | 5.01 | 5.02 | 4.89 | 4.94 |

ND: not determined

The viscosity remains stable whatever the storage conditions and duration.

The concentration of active ingredient (Ia) and the appearance of the gel remain within standards at expiry, whatever the storage conditions and duration, demonstrating the stability of the gel during storage.

The invention claimed is:

1. A pharmaceutical composition including a compound of general formula (I):

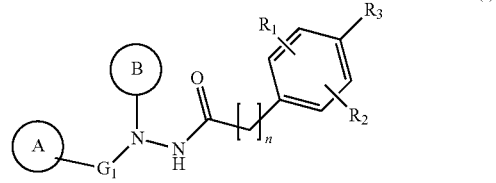

or a pharmaceutically acceptable salt thereof,
wherein:
$G_1$ represents a bond or a linear and saturated hydrocarbon chain comprised of 1 to 4 carbon atoms,
A represents an aryl group optionally substituted:
in the meta or para position by an alkoxy group or by an aryl or arylalkyl group, optionally substituted by one or two substituents, identical or different, selected from the group consisting of acyl and alkoxy,
B represents an aryl group substituted in the ortho position by an N-cycloalkyl, and optionally substituted in the ortho' position by an alkyl group,
n is an integer between 1 and 2,
R1 represents an alkoxy group in the ortho position in relation to R3,
R2 represents a hydrogen or halogen atom, or an alkyl group in the meta position in relation to R3, and
R3 represents an acid group;
in combination with a solvent and a viscosity-enhancing agent, wherein the composition is in gel form, and wherein the gel has a viscosity of 5,000 to 50,000 mPa·s.

2. The pharmaceutical composition according to claim 1, comprising 0.01 to 10% by weight of the compound of formula (I) in relation to the total weight of the pharmaceutical composition.

3. The pharmaceutical composition according to claim 2, comprising 2 to 8% by weight of the compound of formula (I) in relation to the total weight of the pharmaceutical composition.

4. The pharmaceutical composition according to claim 1, wherein the viscosity-enhancing agent is hydroxypropylcellulose, hydroxypropylmethylcellulose, a carbomer or a mixture thereof.

5. The pharmaceutical composition according to claim 4, wherein the viscosity-enhancing agent is hydroxypropylcellulose.

6. The pharmaceutical composition according to claim 1, comprising 0.01 to 50% by weight of viscosity-enhancing agent in relation to the total weight of the pharmaceutical composition.

7. The pharmaceutical composition according to claim 6, comprising 0.5 to 5% by weight of viscosity-enhancing agent in relation to the total weight of the pharmaceutical composition.

8. The pharmaceutical composition according to claim 1, wherein the solvent is propylene glycol, glycerol, polyethylene glycol or a mixture thereof.

9. The pharmaceutical composition according to claim 8, wherein the solvent is propylene glycol.

10. The pharmaceutical composition according to claim 1, comprising 40 to 99.9% by weight of solvent in relation to the total weight of the pharmaceutical composition.

11. The pharmaceutical composition according to claim 10, comprising 85 to 99% by weight of solvent in relation to the total weight of the pharmaceutical composition.

12. The pharmaceutical composition according to claim 11, comprising 90 to 95% by weight of solvent in relation to the total weight of the pharmaceutical composition.

13. The pharmaceutical composition according to claim 1, including, in relation to the total weight of the pharmaceutical composition:
0.01 to 10% by weight of the compound of formula (I),
0.01 to 50 by weight of viscosity-enhancing agent, and
40 to 99.9% by weight of solvent.

14. The pharmaceutical composition according to claim 13, including, in relation to the total weight of the pharmaceutical composition:
0.01 to 10% by weight of the compound of formula (I),
0.05 to 10% by weight of a viscosity-enhancing agent selected from hydroxypropylcellulose, hydroxypropylmethylcellulose, a carbomer and mixtures thereof, and
80 to 99.5% by weight of a solvent selected from propylene glycol, glycerol, polyethylene glycol and mixtures thereof.

15. The pharmaceutical composition according to claim 14, having the following composition in relation to the total weight of the pharmaceutical composition:
0.01 to 10% by weight of the compound of formula (I),
0.05 to 10% by weight of hydroxypropylcellulose, and
80 to 99.5% by weight of propylene glycol.

16. The pharmaceutical composition according to claim 15, having the following composition in relation to the total weight of the pharmaceutical composition:
2 to 8% by weight of the compound of formula (I),
0.5 to 5% by weight of hydroxypropylcellulose, and
90 to 95% by weight of propylene glycol.

17. The pharmaceutical composition according to claim 1, wherein the gel has a viscosity of 15,000 to 25,000 mPa·s.

18. The pharmaceutical composition according to claim 1, wherein the compound of formula (I) has the following features:
A represents a phenyl group substituted in the para position by a benzyl group,
B represents a phenyl group substituted in the ortho position by a piperidin-1-yl group and in the ortho' position by a methyl group, and
G1 represents a bond.

19. The pharmaceutical composition according to claim 1, wherein the compound of formula (I) is 4-[N'-(4-benzyl-phenyl)-N'-(2-methyl-6-piperidin-1-yl-phenyl)-hydrazinocarbonylmethyl]-5-bromo-2-methoxy-benzoic acid or a pharmaceutically acceptable salt thereof.

20. The pharmaceutical composition according to claim 19, wherein the compound of formula (I) is the potassium salt of 4-[N'-(4-benzyl-phenyl)-N'-(2-methyl-6-piperidin-1-yl-phenyl)-hydrazinocarbonylmethyl]-5-bromo-2-methoxy-benzoic acid.

21. A method for preparing a pharmaceutical composition according to claim 1, comprising the following steps:
i) mixing the compound of formula (I) in a part of the solvent to yield a solution A,
ii) mixing the viscosity-enhancing agent in the remaining part of the solvent to yield a solution B, and
iii) mixing solutions A and B to yield the pharmaceutical composition.

22. A method for treating papillomavirus infection comprising the administration to a person in need thereof of an effective amount of a pharmaceutical composition according to claim 1.

23. The method according to claim 22, wherein the papillomavirus infection is an HPV6 or HPV11 infection.

24. A method for treating lesions or diseases associated with papillomavirus infections comprising administration to a person in need thereof of an effective amount of a pharmaceutical composition according to claim 1.

25. The method according to claim 24, wherein the lesions or diseases associated with papillomavirus infections are selected from anogenital warts, laryngeal, conjunctival or oral papillomas, recurrent respiratory papillomatosis, low-grade and high-grade intraepithelial neoplasia, bowenoid papulosis, common, plantar, myrmecia, superficial or flat warts, epidermodysplasia verruciformis, and carcinomas.

26. The method according to claim 24, wherein the lesions or diseases associated with papillomavirus infections are selected from condyloma acuminata and condyloma lata.

* * * * *